US008529765B2

(12) United States Patent
Horton (10) Patent No.: US 8,529,765 B2
(45) Date of Patent: Sep. 10, 2013

(54) ENSILING BIOMASS FOR BIOFUELS PRODUCTION AND MULTIPLE PHASE APPARATUS FOR HYDROLYZATION OF ENSILED BIOMASS

(75) Inventor: Jerry Wayne Horton, Rush, NY (US)

(73) Assignee: Sweetwater Energy, Inc., Rochester, NY (US)

(*) Notice: Subject to any disclaimer, the term of this patent is extended or adjusted under 35 U.S.C. 154(b) by 589 days.

(21) Appl. No.: 12/633,555

(22) Filed: Dec. 8, 2009

(65) Prior Publication Data

US 2010/0144001 A1 Jun. 10, 2010

Related U.S. Application Data

(60) Provisional application No. 61/201,205, filed on Dec. 9, 2008.

(51) Int. Cl.
*C02F 1/66* (2006.01)
*B01D 11/00* (2006.01)
*C08B 30/04* (2006.01)
*C08B 30/06* (2006.01)
*C12M 1/00* (2006.01)
*C12P 7/06* (2006.01)

(52) U.S. Cl.
USPC ............ 210/632; 100/37; 100/38; 100/43; 127/1; 127/36; 127/37; 127/65; 127/67; 127/69; 127/71; 210/639; 210/651; 210/652; 210/739; 210/749; 210/770; 210/774; 210/787; 210/806; 210/808

(58) Field of Classification Search
USPC ............ 210/143, 149, 202, 205, 209, 241, 210/257.1, 257.2, 259, 177, 182, 632, 639, 210/651, 652, 739, 749, 757, 758, 770, 774, 210/787, 806, 808; 44/302, 307, 588, 589, 44/605, 606; 127/1, 23, 24, 37, 36, 65, 67, 127/69, 71; 435/134–136; 100/43, 70 R, 100/71, 73–75, 90, 92, 308, 309, 37, 38
See application file for complete search history.

(56) References Cited

U.S. PATENT DOCUMENTS 4,048,341 A 9/1977 Lagerstrom et al.
4,070,232 A 1/1978 Funk
(Continued)

FOREIGN PATENT DOCUMENTS

CA 1267407 B 4/1990
EP 1259466 B1 10/2008
(Continued)

OTHER PUBLICATIONS

PCT International Search Report and Written Opinion for International Application No. PCT/US 09/67221; Date of Mailing Jan. 26, 2009. 7 pages.
(Continued)

*Primary Examiner* — Joseph Drodge
(74) *Attorney, Agent, or Firm* — Wilson Sonsini Goodrich & Rosati (57) ABSTRACT

A method, apparatus and system for the hydrolyzation of ensiled biomass is disclosed. Ensiled biomass is processed in multiple phases, resulting in a liquid precursor hydrozate and a solid precursor hydrozate. The liquid precursor having significant economic value, and being suitable for uses such as, for example, lower cost and improved efficiency ethanol production. A method for lower cost, improved efficiency alcohol production that uses the resulting liquid precursor hydrozate being produced at distributed sources is further disclosed.

18 Claims, 11 Drawing Sheets

(56) References Cited

U.S. PATENT DOCUMENTS

| | | | |
|---|---|---|---|
| 4,182,780 A | 1/1980 | Lagerstrom et al. | |
| 4,201,596 A | 5/1980 | Church et al. | |
| 4,350,766 A | 9/1982 | Mehlberg | |
| 4,395,488 A | 7/1983 | Rowe | |
| 4,414,330 A | 11/1983 | Zucker et al. | |
| 4,447,534 A | 5/1984 | Moebus et al. | |
| 4,478,854 A | 10/1984 | Adler-Nissen et al. | |
| 4,520,105 A | 5/1985 | Sinner et al. | |
| 4,600,590 A | 7/1986 | Dale | |
| 4,612,286 A | 9/1986 | Sherman et al. | |
| 4,615,742 A | 10/1986 | Wright | |
| 4,644,060 A | 2/1987 | Chou | |
| 4,650,689 A | 3/1987 | Hedrick | |
| 4,806,475 A | 2/1989 | Gould | |
| 5,037,663 A | 8/1991 | Dale | |
| 5,144,008 A | 9/1992 | Ikeda et al. | |
| 5,171,592 A | 12/1992 | Holtzapple et al. | |
| 5,177,008 A | 1/1993 | Kampen | |
| 5,177,009 A | 1/1993 | Kampen | |
| 5,338,366 A * | 8/1994 | Grace et al. | 127/37 |
| 5,454,911 A * | 10/1995 | Rafferty | 162/247 |
| 5,473,061 A | 12/1995 | Bredereck et al. | |
| 5,693,296 A | 12/1997 | Holtzapple et al. | |
| 5,726,046 A | 3/1998 | Farone et al. | |
| 5,846,787 A | 12/1998 | Ladisch et al. | |
| 5,865,898 A | 2/1999 | Holtzapple et al. | |
| 5,916,780 A | 6/1999 | Foody et al. | |
| 5,939,544 A | 8/1999 | Karstens et al. | |
| 5,969,189 A | 10/1999 | Holtzapple et al. | |
| 5,986,133 A | 11/1999 | Holtzapple et al. | |
| 6,043,392 A | 3/2000 | Holtzapple et al. | |
| 6,106,888 A | 8/2000 | Dale et al. | |
| 6,176,176 B1 | 1/2001 | Dale et al. | |
| 6,258,175 B1 | 7/2001 | Lightner | |
| 6,262,313 B1 | 7/2001 | Holtzapple et al. | |
| 6,332,542 B2 | 12/2001 | Bilodeau et al. | |
| 6,365,732 B1 | 4/2002 | Van Thorre | |
| 6,416,621 B1 | 7/2002 | Karstens | |
| 6,478,965 B1 | 11/2002 | Holtzapple et al. | |
| 6,509,180 B1 | 1/2003 | Verser et al. | |
| 7,109,005 B2 | 9/2006 | Eroma et al. | |
| 7,198,925 B2 | 4/2007 | Foody | |
| 7,503,981 B2 | 3/2009 | Wyman et al. | |
| 7,807,419 B2 | 10/2010 | Hennessey et al. | |
| 7,909,895 B2 * | 3/2011 | Dickinson et al. | 44/307 |
| 7,932,063 B2 | 4/2011 | Dunson, Jr. et al. | |
| 7,932,065 B2 | 4/2011 | Medoff | |
| 7,935,840 B2 * | 5/2011 | Leveson et al. | 554/170 |
| 8,103,385 B2 * | 1/2012 | Macharia et al. | 700/282 |
| 8,123,864 B2 * | 2/2012 | Christensen et al. | 127/37 |
| 8,168,840 B2 | 5/2012 | Brady et al. | |
| 8,323,923 B1 | 12/2012 | Horton | |
| 8,328,947 B2 | 12/2012 | Anand et al. | |
| 2002/0038058 A1 | 3/2002 | Holtzapple et al. | |
| 2002/0164730 A1 | 11/2002 | Ballesteros Perdices et al. | |
| 2002/0164731 A1 | 11/2002 | Eroma et al. | |
| 2002/0192774 A1 | 12/2002 | Ahring et al. | |
| 2002/0197686 A1 | 12/2002 | Lightner | |
| 2003/0199049 A1 | 10/2003 | Nguyen et al. | |
| 2003/0221361 A1 | 12/2003 | Russell et al. | |
| 2003/0224088 A1 | 12/2003 | Burdick | |
| 2004/0152881 A1 | 8/2004 | Holtzapple et al. | |
| 2004/0168960 A1 | 9/2004 | Holtzapple et al. | |
| 2004/0171136 A1 | 9/2004 | Holtzapple et al. | |
| 2005/0054064 A1 | 3/2005 | Talluri et al. | |
| 2005/0244934 A1 | 11/2005 | Foody et al. | |
| 2005/0272134 A1 | 12/2005 | Hughes | |
| 2006/0003064 A1 | 1/2006 | James | |
| 2006/0024801 A1 | 2/2006 | Holtzapple et al. | |
| 2006/0069244 A1 | 3/2006 | Holtzapple et al. | |
| 2006/0188980 A1 | 8/2006 | Holtzapple et al. | |
| 2006/0251764 A1 | 11/2006 | Abbas et al. | |
| 2007/0037259 A1 | 2/2007 | Hennessey et al. | |
| 2007/0118916 A1 | 5/2007 | Puzio et al. | |
| 2007/0148750 A1 | 6/2007 | Hoshino et al. | |
| 2007/0190626 A1 | 8/2007 | Wilkening et al. | |
| 2007/0275447 A1 | 11/2007 | Lewis et al. | |
| 2008/0014617 A1 | 1/2008 | Cerea | |
| 2008/0121359 A1 | 5/2008 | Holtzapple et al. | |
| 2009/0042259 A1 | 2/2009 | Dale et al. | |
| 2009/0043686 A1 | 2/2009 | Matsumoto | |
| 2009/0064566 A1 * | 3/2009 | Brummerstedt Iversen et al. | 44/307 |
| 2009/0098617 A1 | 4/2009 | Burke et al. | |
| 2009/0298149 A1 | 12/2009 | Wang et al. | |
| 2010/0021980 A1 | 1/2010 | McDonald et al. | |
| 2010/0055741 A1 | 3/2010 | Galvez, II et al. | |
| 2010/0221819 A1 | 9/2010 | Foody et al. | |
| 2010/0227369 A1 | 9/2010 | Narendranath et al. | |
| 2010/0317053 A1 | 12/2010 | Stromberg et al. | |
| 2011/0079219 A1 * | 4/2011 | McDonald et al. | 127/1 |
| 2011/0081689 A1 | 4/2011 | Flanegan et al. | |
| 2011/0114765 A1 | 5/2011 | Brady et al. | |
| 2011/0129886 A1 | 6/2011 | Howard et al. | |
| 2011/0201084 A1 | 8/2011 | Wyman et al. | |
| 2011/0258911 A1 * | 10/2011 | Hanson et al. | 44/307 |
| 2011/0258913 A1 | 10/2011 | Stamires et al. | |
| 2012/0006320 A1 | 1/2012 | Nguyen | |
| 2012/0041186 A1 | 2/2012 | Pschorn et al. | |
| 2012/0100577 A1 | 4/2012 | Medoff et al. | |
| 2012/0122162 A1 | 5/2012 | Romero et al. | |
| 2012/0190092 A1 | 7/2012 | Jaquess et al. | |
| 2012/0214216 A1 | 8/2012 | Brady et al. | |

FOREIGN PATENT DOCUMENTS

| | | |
|---|---|---|
| EP | 1307735 B1 | 11/2008 |
| EP | 1299170 B1 | 8/2010 |
| JP | 2006-149343 A | 6/2006 |
| WO | WO 01/32715 A1 | 5/2001 |
| WO | WO 01/60752 A1 | 8/2001 |
| WO | WO 02/00324 A1 | 1/2002 |
| WO | WO 02/01220 A2 | 1/2002 |
| WO | WO 02/01220 A3 | 9/2002 |
| WO | WO 2004/081193 A2 | 9/2004 |
| WO | WO 2005/087937 A2 | 9/2005 |
| WO | WO 2005/118828 A1 | 12/2005 |
| WO | WO 2009/063138 A2 | 5/2009 |
| WO | WO 2010/056940 A2 | 5/2010 |
| WO | WO 2011/103033 A1 | 8/2011 |
| WO | WO 2012/051523 A1 | 4/2012 |
| WO | WO 2012/099967 A1 | 7/2012 |

OTHER PUBLICATIONS

Dr. Hossein Shapouri and Dr. Michael Salassi, "The Economic Feasibility of Ethanol Production From Sugar in the United States", Report, Jul. 2006, 78 pages, USDA, USA.

Office action dated Feb. 20, 2013 for U.S. Appl. No. 13/686,477.

U.S. Appl. No. 13/646,425, filed Oct. 5, 2012, Horton.

U.S. Appl. No. 13/793,860, filed Mar. 11, 2013, Horton.

Alcohol and Tobacco Tax and Trade Bureau, treasury. 27 C.F.R. §19.134 Bonded warehouse not on premises qualified for production of spirits, p. 381, Apr. 1, 1997 revision.

Boggan. 2003. Alcohol, Chemistry and You Sources and Uses of Ethyl Alcohol. Kennesaw State University, pp. 1-5, Printed May 17, 2010. http://www.chemcases.corn/alcohol/alc-03.htm/.

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

Dowe, et al (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages).

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Gibreel, et al. Fermentation of barley by using *Saccharomyces cerevisiae*: examination of barley as a feedstock for bioethanol production and value-added products. Appl Environ Microbiol. Mar. 2009;75(5):1363-72. doi: 10.1128/AEM.01512-08. Epub Dec. 29, 2008.

Gum, et al. Structural characterization of a glycoprotein cellulase, 1,4-beta-D-glucan cellubiohydrolase C from trichodermaviride. Biochem. Biophys. Acta. 1976; 446:370-86.

Jones, et al. (1994, Ethanolic Fermentation of Blackstrap Molasses and Sugarcane Juice Using Very High Gravity Technology. J. Agric. Food Chem, vol. 42, pp. 1242-1246).

Kim, et al. Lime pretreatment and enzymatic hydrolysis of corn stover. Bioresour Technol. Dec. 2005;96(18):1994-2006.

Kim, et al. Pretreatment and fractionation of corn stover by ammonia recycle percolation process. Bioresour Technol. Dec. 2005;96(18):2007-13.

Lloyd, et al. Combined sugar yields for dilute sulfuric acid pretreatment of corn stover followed by enzymatic hydrolysis of the remaining solids. Bioresour Technol. Dec. 2005;96(18):1967-77.

Mosier, et al. Features of promising technologies for pretreatment of lignocellulosic biomass. Bioresour Technol. Apr. 2005;96(6):673-86.

Mosier, et al. Optimization of pH controlled liquid hot water pretreatment of corn stover. Bioresour Technol. Dec. 2005;96(18):1986-93.

Nevoigt, et al. Osmoregulation and glycerol metabolism in the yeast *Saccharomyces cerevisiae*. FEMS Microbial Rev. Nov. 1997;21(3):231-41.

Notice of allowance dated Oct. 15, 2012 for U.S. Appl. No. 11/974,129.

Office action dated May 24, 2010 for U.S. Appl. No. 11/974,129.

Office action dated Jul. 6, 2012 for U.S. Appl. No. 11/974,129.

Office action dated Nov. 8, 2010 for U.S. Appl. No. 11/974,129.

Parekh, et al. Production of glycerol by hansenula anomala. Biotechnol Bioeng. Jul. 1985;27(7):1089-91.

Santoro, et al. A High-throughput Platform for Screening Milligram Quantities of Plant Biomass for Lignocellulose Digestibility. Bioenerg. Res. Jan. 2010; 3:93-102.

Sluiter, et al. Determination of structural carbohydrates and lignin in biomass. National Renewable Energy Laboratory. Technical report NREL/TP-510-42618. Revised Jun. 2010.

Taylor. From Raw Sugar to Raw materials. Chemical innovation. 2000; 30:45-48.

USDA, "The Economic Feasibility of Ethanol Production From Sugar in the United States"; Jul. 2006, 69 pages.

Varhegyi, et al. (1989. Kinetics of the thermal decomposition of cellulose, hemicellulose, and sugarcane bagasse. Energy Fuels, vol. 3, No. 3, pp. 329-335).

Waiss, et al. Improving Digestibility of Straws for Ruminant Feed by Aqueous Ammonia. Journal of Animal Science. 1972; 35(1):109-112.

Waltermann, et al. *Rhodococcus opacus* strain PD630 as a new source of high-value single-cell oil? Isolation and characterization of triacylglycerols and other storage lipids. Microbiology. 2000; 146:1143-1149.

International search report and written opinion dated May 30, 2013 for PCT/US2013/025457.

International search report and written opinion dated Jun. 20, 2013 for PCT/US2013/036497.

* cited by examiner

ENSILING BIOMASS FOR BIOFUELS PRODUCTION AND MULTIPLE PHASE APPARATUS FOR HYDROLYZATION OF ENSILED BIOMASS

CROSS-REFERENCE TO RELATED PATENT APPLICATIONS

This application claims the benefit of the filing date of U.S. Provisional patent application Ser. No. 61/201,205 filed on Dec. 9, 2008.

BACKGROUND OF THE INVENTION

1. Field of the Invention

The present invention relates to biofuels production, and more particularly, relates to an apparatus, system and method for manufacturing liquid precursors and solid precursors.

2. Description of Related Art

The production of alcohol such as ethanol frequently uses corn as a feedstock and requires high energy input, typically from fossil fuels. Ethanol holds promise as a fuel source that is not petroleum based; a desirable goal for the United States and other countries seeking energy independence and lower environmental impact. Unfortunately ethanol production in the United States has come under scrutiny due to the need for large amounts of fossil fuel to both process the ethanol and also to ship the feedstock to a central refinery.

There exists an unmet need for improved processes, methods, systems and equipment to produce biofuels such as alcohols, for example ethanol, with power energy input demands. This reduction in energy use can come from various improvements including process improvements at the biorefinery as well as improvements in feedstock production, processing and transportation. These improvements are necessary if ethanol and related biofuels are to become a viable long term source of transportation fuel and transportation fuel additives.

In the United States corn is the primary feedstock for ethanol production due to the climate and available growing conditions. To make a biorefinery cost effective, feedstock should be available year round to maintain continuous production and ensure proper and adequate utilization of plant and equipment. Storage of feedstock becomes a necessity to meet these operating objectives. Unfortunately storage of feedstock represents additional costs both in storage and transportation, serving to further misalign the cost targets of ethanol production. There exists an unmet need for improved feedstock storage and processing to reduce the overall costs of ethanol and related biofuel production.

It is thus an object of the present invention to provide an improved feedstock processing and storage system. It is another object of the present invention to provide an apparatus to produce liquid precursors for biofuels production such as alcohols, for example, ethanol. It is another object of the present invention to provide an apparatus that separates liquid precursors from solid precursors. It is another object of the present invention to provide a method for producing biofuels that uses a liquid precursor from a plurality of distributed sources. It is yet another object of the present invention to provide a method for producing biofuels that reduces transportation costs from the feedstock source to the biorefinery. It is another object of the present invention to provide a method and apparatus for biofuels production that reduces process energy use. It is yet another object of the present invention to provide a method and apparatus for producing solid precursors from feedstock that have utility and are environmentally benign. It is another object of the present invention to provide a method and system for producing biofuels that reduces feedstock storage requirements at the biorefinery. It is yet another object of the present invention to provide a method, system and apparatus that reduces the size, cost and operating energy usage of a biorefinery.

These and other objects of the present invention are described in the detailed specification, drawings and claims contained herein.

BRIEF SUMMARY OF THE INVENTION

In accordance with the present invention, there is provided a multiple phase apparatus for the hydrolyzation of ensiled biomass that results in a solid precursor and a liquid precursor, the liquid precursor having significant economic value, and being suitable for uses such as for example, lower cost and improved efficiency ethanol production. The solid precursor also having economic value and utility. The resulting liquid precursor being produced at a plurality of distributed sources and shipped to a biorefinery for production of biofuel such as ethanol.

The foregoing paragraph has been provided by way of introduction, and is not intended to limit the scope of the invention as described and claimed herein.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, drawings, and claims contained herein.

DESCRIPTION OF THE PREFERRED EMBODIMENTS

For a general understanding of the present invention, reference is made to the drawings. In the drawings, like reference numerals have been used throughout to designate identical elements.

As used herein, the term "liquid precursor hydrozate" shall refer to a liquid derived from ensiled biomass and water that has been processed and otherwise treated as disclosed or suggested herein.

As used herein, the term "feedstock" shall refer to any and all biomass, such as, but not limited to, hard grains, starches, cellulose, hemicellulose and lignocellulosic biomasses such as corn stover, cereal straws, sugarcane bagasse, sawdust and paper pulp, waste materials, switchgrass, old and/or poor quality animal feed, paper, cardboard, other biomass derivatives, complete plant materials, and any material or substance that may be used to produce biofuels such as ethanol. Feedstock has also been referred to herein as biomass, and the terms are used interchangeably throughout this specification.

The terms hydrolyze and hydrolyzation refer to the process of adding water to a material such as, for example, ensiled and processed biomass. The term hydrozate refers to a product of hydrolyzation according to the present invention, and may be a liquid hydrozate or a solid hydrozate, and is also referred to in this specification as a liquid precursor hydrozate or a solid precursor hydrozate. A liquid precursor hydrozate may contain solids and a solid precursor hydrozate may contain liquids; the term liquid precursor hydrozate indicates that the material is primarily liquid in composition and the term solid precursor hydrozate indicates that the material is primary solid in composition.

A liquid precursor hydrozate is produced, as will be further described herein. This liquid precursor hydrozate has undergone processing and may undergo further processing such that it is suitable for biofuels such as alcohol, for example ethanol production. The liquid precursor hydrozate is shipped from distributed locations to central biorefineries where processes may include fermentation and distillation to make the final product.

At each distributed location, in addition to the production of liquid precursor hydrozates, solid precursor hydrozates are co-products that may be used for absorbent media animal or human food and food additives, building products such as composite boards and sheets, animal bedding, combustible fuels such as burning pellets, adhesive and plastic additives, bio-plastics, soil additives, and the like.

Figure 1:
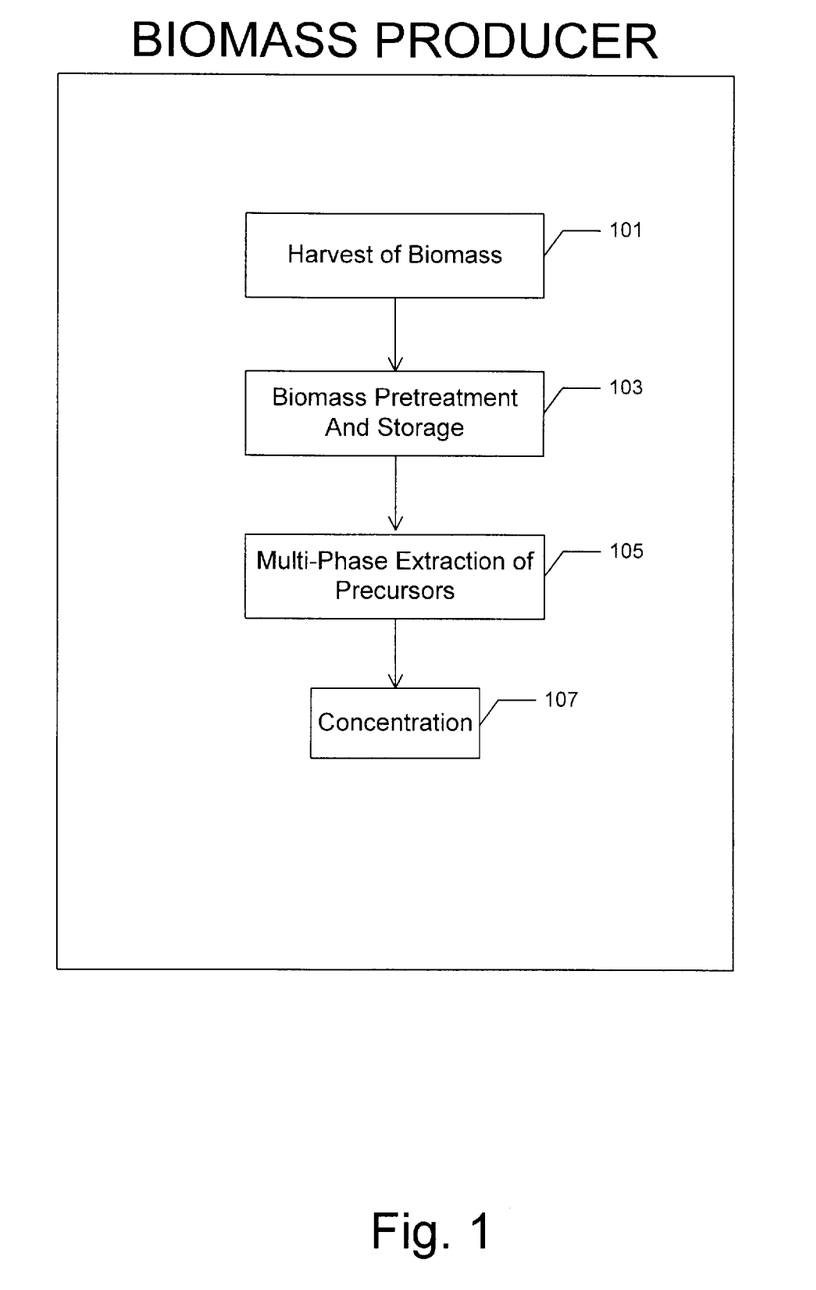
FIG. 1 is a diagram depicting processes at a biomass producer.

FIG. 1 is a diagram depicting processes at a biomass producer. Biomass producers are at distributed locations that may be local or regional. The biomass producer may be the grower of the biomass, or may use biomass that has been grown for other purposes. The biomass may, in some embodiments of the present invention, be processed or otherwise modified prior to use in the production of liquid precursor hydrozates. The biomass may be a by-product of another product or process. A biomass producer includes feedstock producers as well as feedstock processors, feedstock storage facilities, food processors, recycling centers, and the like. Feedstock may include hard grains, cellulose biomasses, waste materials, biomasses farmed for the sole purpose of producing biofuels such as alcohol, for example ethanol, old and/or poor quality animal feed, and the like. Feedstock includes any material or substance that may be used to produce biofuels for example alcohol. In FIG. 1, harvest of biomass is performed in step 101. Harvest step 101 will be further discussed by way of FIG. 2. Biomass includes feedstock as well as other biologically occurring materials that may be in their natural state, or may have been processed or otherwise altered by acts of man. This includes, for example, biomass as a by product, waste product, or secondary product of food or material production. Thus, harvest includes not only direct removal of organic material from cropland, but also includes collecting or harvesting biomass from other sources that may include, for example, marine sources, production and manufacturing sources, storage and processing sources, recycling sources, and the like.

In FIG. 1, once the biomass is harvested, a pretreatment and storage step 103 takes place. Pretreatment and Storage will be further discussed in FIG. 3. Pretreatment may include mechanical reformation and processing of the feedstock such as mechanical destruction, reformation, grinding, chopping, shredding, crushing or separating of the feedstock. Pretreatment may also include the addition or removal of water or other chemicals, and may include the addition of innoculates. Once pretreatment of the biomass is performed, the biomass is stored in a high moisture state in traditional or modified feed storage structures such as silos, bins, inground bunkers, ag bags, and the like. The anaerobic storage of high moisture biomass is known as ensiling. Ensiled biomass provides a material to manufacture liquid precursor hydrozates many months after the growing season is over, thus allowing year round production and load balancing of biorefineries. The biomass can be pretreated in step 103 of FIG. 1 to allow for optimal efficiency liquid precursor hydrozate production. Once the biomass has been pretreated and stored in step 103, it can be used in the production of a liquid precursor hydrozate, which is a non-fermented, high sugar content liquid that has been derived from the ensiled biomass using processes and methods that will be further described by way of FIG. 4. The multi-phase extraction of precursors in step 105 may take place weeks or months after the biomass is pretreated and stored in step 103. The multi-phase extraction of precursors in step 105, as will be further described by way of FIG. 4, involves the production of liquid precursor hydrozate as well as solid precursor hydrozate that also has utility for purposes such as absorbent media, animal or human food and food additives, building products such as composite boards and sheets, animal bedding, combustible fuels such as burning pellets, adhesive and plastic additives, bio-plastics, and the like. Step 107 is a Concentration step where the liquid precursor hydrozate undergoes water removal using techniques such as reverse osmosis ultra or nano filtration, heat, and the like. Step 107 of FIG. 1 is further described by way of FIG. 5.

Figure 2:
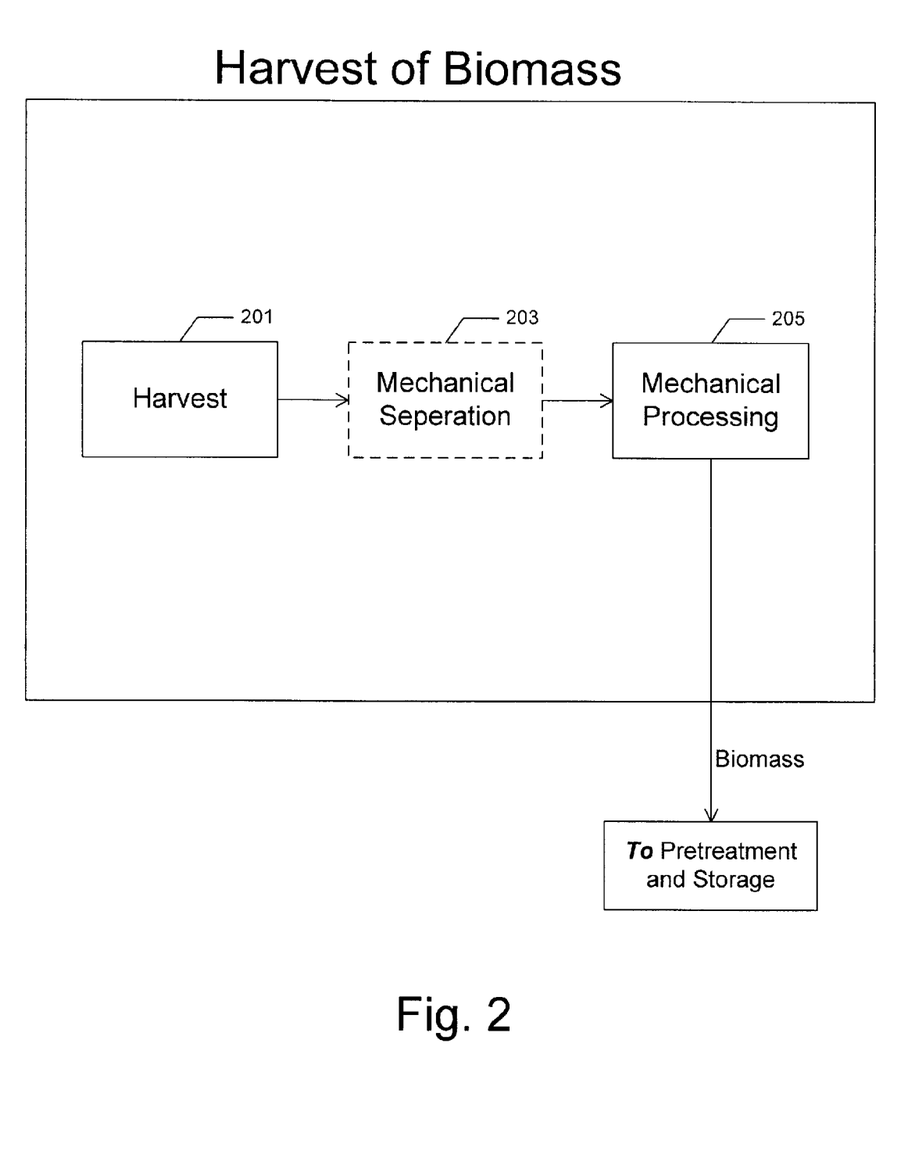
FIG. 2 is a diagram depicting steps taken during harvest of biomass.

Turning now to FIG. 2, the Harvest step 101 of FIG. 1 is further described. Harvesting of biomass includes not only direct removal of organic material from cropland, but also includes collecting or harvesting biomass from other sources that may include, for example, marine sources, production and manufacturing sources, storage and processing sources, and the like. Biomass includes feedstock taken from cropland, as well as other biologically occurring materials that may be in their natural state, or may have been processed or otherwise altered by acts of man. This includes, for example, biomass as a by-product, waste product, or secondary product of food or material production.

An optional mechanical separation step 203 involves sorting or otherwise segregating the harvested biomass. For example, corn may be separated into constituent materials such as stalks, cobs and kernels. Mechanical separation may be used to enhance the production of liquid precursor hydrozate, or may be used to segregate constituent agricultural products that may be used for various other purposes. Mechanical processing 205 of the biomass may include mechanical destruction, reformation, grinding, chopping, shredding, crushing, separating, or other mechanical actions intended to render the feedstock more suitable for the manufacture of liquid precursor hydrozate. Once the biomass is harvested, optionally separated, and processed, Pretreatment and Storage of the Biomass is performed.

Figure 3:
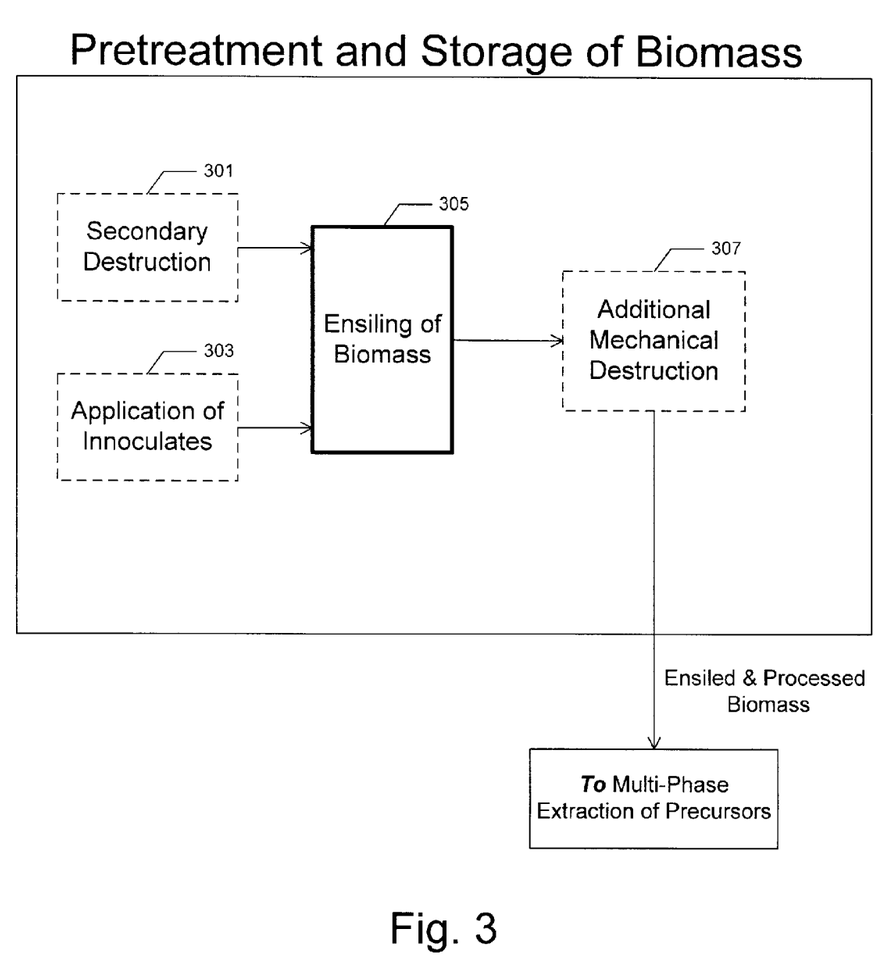
FIG. 3 is a diagram that illustrates steps taken during pretreatment and storage of biomass.

Turning to FIG. 3 an optional secondary destruction 301 may take place that may include mechanical destruction, reformation, grinding, chopping, shredding, crushing, separating, or other mechanical actions intended to render the biomasss more suitable for the manufacture of liquid precursor hydrozate. Optionally there may also be an application of innoculates 303. Inoculants may include, for example, lactic acid bacteria inoculants. Examples of lactic acid bacteria inoculants include, for example, Biomax® by Chr. Hansen A/S of Hørsholm, Denmark, Biotal Plus® by Lallemand Animal Nutrition of Milwaukee, Wis., USA and Rexdale, Ontario, Canada, Biotal® and Biotal Plus II® by Lallemand Animal Nutrition of Milwaukee, Wis., USA, Pioneer® brand 11A44 inoculant by Pioneer Hi-Bred International, Inc. of Johnston, Iowa, USA, Pioneer® brand 11GFT inoculant by Pioneer Hi-Bred International, Inc. of Johnston, Iowa, USA, Kern LAC® Brand HD by Kemin Industries, Inc. of Des Moines, Iowa, USA, FermenAider™ by Bio-Vet, Inc. of Blue Mounds, Wis., SA, Sil-All® 4X4WS by AllTech of Lexington, Ky., USA, Lactisil H/MF Inoculant by Canadian Bio-Systems Inc. of Calgary, Alberta, Canada, and ECOSYL 66 by ECOSYL Products Limited based at Stokesley in North Yorkshire, United Kingdom.

The biomass is then ensiled in step 305. The anaerobic storage of high moisture biomass is known as ensiling. Storage may be in traditional or modified feed storage structures such as silos, bins, and the like. Ensiled biomass can be stored long term, and provides a material to manufacture liquid precursor hydrozates, thus allowing year round production and load balancing of biorefineries. Liquid precursor hydrozate is a non-fermented, high sugar content liquid that has been produced from the ensiled biomass. Ensiling is an anaerobic fermentation process used to preserve the complete plant material of, for example, immature green corn, legumes, grasses, grain plants and food processing waste. Ensiling may include chopping or mechanically processing the biomass and packing it with high moisture content in silos or other containment structures to exclude air. Shortly after the introduction of the biomass some of the oxygen in the plant material will lead to respiration in the plant cells during the formation of carbon dioxide and heat. The respiration takes place at the expense of readily digestible carbohydrates. Besides the plant cells, facultative anaerobic and aerobic micoorganisms will also take part in this process. In the second phase coliforme bacteria and other bacteria produce small amounts of acetic acid. This phase is of short duration. In the third phase lactic acid bacteria will convert readily digestible carbohydrates into lactic acid. In the fourth phase a stable state of equilibrium is achieved in the mass with an approximately constant lactic acid content and contant pH. The first three phases usually take from 3 to 5 days and the fourth phase will usually take from 2 to 3 weeks. Ensiling is used for long term storage as well as preconditioning of plant material (biomass) for the purpose of processing it into lignocellulosic based biofuel. Prior to production of liquid precursor hydrorate, the ensiled biomass may undergo an optional additional mechanical destruction step 307 that may include chopping, shredding, grinding, or other mechanical processing.

The ensiled and processed biomass now can be used for multi-phase extraction of precursors. This is further described by way of FIG. 4, and is a highly flexible multiple phase modular processing system used to convert ensiled biomass into liquid precursor hydrozates and solid precursor hydrozates. The number of phases and the number of modules required at any given time depends on the incoming feedstock, feedstock processing rate and the resulting coproducts desired. The system and multi phase apparatus is flexible in processing capacity and can be portable, or may also be operated as a fixed system. Each phase begins with solid biomass and the addition of phase specific aqueous based reagant solution depending on the targetted coproducts. The phases are completed in series with the previous one producing the solid feedstock biomass that may be sold or used as the solid biomass fraction for the next phase. Depending on the biomass being produced each of the phases can have multiple steps and these steps may or may not be repeated within any given phase. There is the possibility of three different liquid precursor hydrozates being produced and three different biomass solids being produced depending on the supplied biomass and the desired resulting products. Each of the three phases produces a liquid precursor hydrozate and a solid precursor hydrozate which may be sold as is or used as a feedstock for the next phase. Each step of each phase may be a batch process or a continuous process depending on the feedstock and system requirements. As will be further described, each of the three phases may be run in series, repeated, run in varying order, or omitted and substituted based on operational requirements such as biomass properties, end product specifications, and the like.

Figure 4:
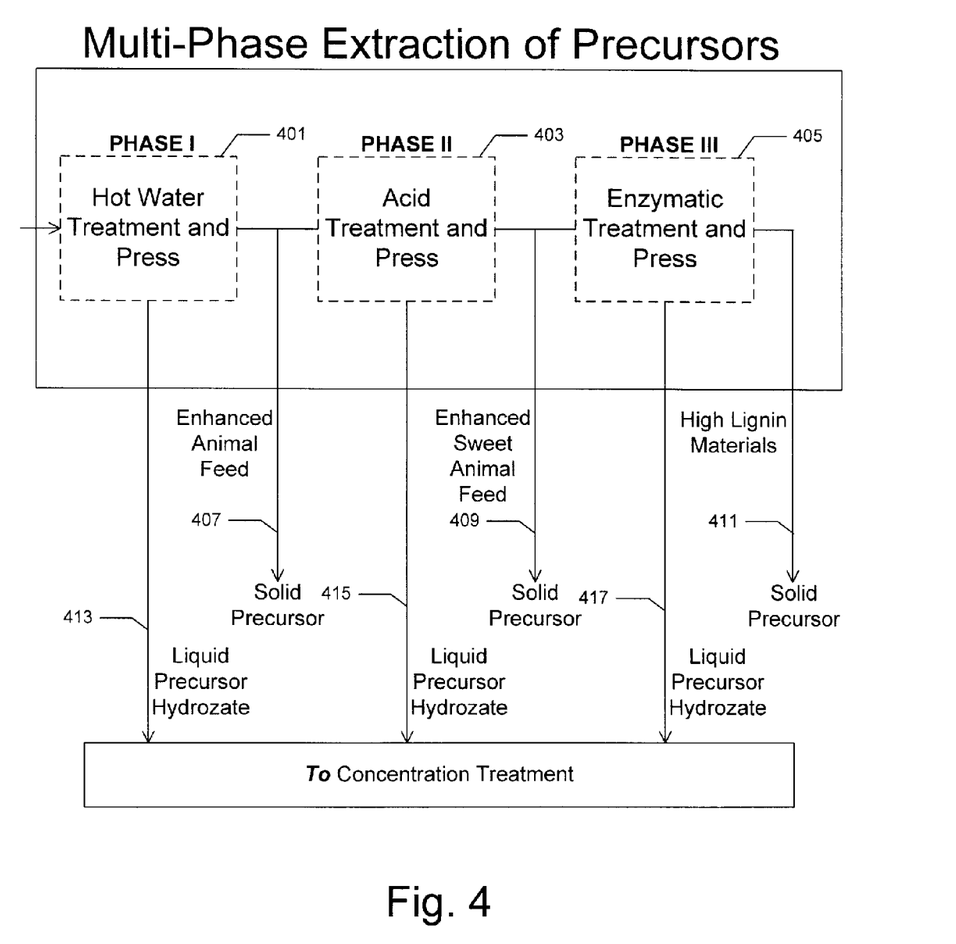
FIG. 4 is a diagram that illustrates multi-phase extraction of precursors.

Phase I involves a hot water treatment and press 401. Hot water treatment may involve multiple cycles where, in some embodiments of the present invention, liquid from the second extraction cycle is reused in the repeated first cycle. Multiple cycles may or may not be used dependent on the final coproducts being produced. In an extraction cycle, aqueous solution, or in a multi cycle approach liquid from a previous cycle, is added to mechanically conditioned and ensiled (or other) solid fraction along with additional additives resulting in an aqueous liquid fraction and a lower moisture solid fraction. After a given period of time at a required temperature the first phase hydrolyzes the free carbohydrates along with other known soluble materials. In many embodiments of the present invention, the first extraction liquid and the last extraction solid of phase I are the finished coproduct objectives. Phase I may involve continuous or batch processing depending on operational factors such as the biomass being processed and the processing time requirements. Once hot water treatment is completed, the saturated material is pressed. For purposes of this specification, press includes any action taken on the saturated material (hot water treated biomass) to enhance the extraction of liquid precursor hydrozate. This may include, but is not limited to, mechanical pressing, cetrifuge, gravity, and the like. When pressed, the treated biomass yields a liquid precursor hydrozate 413 that is placed in a vessel or other storage device for later processing and shipment to a user of the liquid, such as a biorefinery. The solids remaining may then be used for applications such as, but not limited to, enhanced animal feed, or they may be further processed in Phase II. Phase II involves an acid treatment and press 403. This second phase is an optional phase of the multiple phase apparatus and may or may not be required depending on the biomass being produced and the co-products being required or requested. Phase II can be run on equipment similar to that used for Phase I. The primary objective of Phase II is to hydrolyze and extract carbohydrates that require processing at lower pH levels, allowing production of economical hydrozate. As with Phase I, Phase II may involve multiple cycles. A first cycle may use aqueous solution with pH adjusting additives as a liquid fraction or previous cycle extraction liquid along with additional pH adjusting additives as a liquid fraction. Acids that may be used in acid treatment include, but are not limited to, sulfuric acid, muriatic acid, hydrochloric acid, and the like. The solid fraction biomass is typically the solids coproduced in Phase I. After a given period of time at a required temperature the second phase Hydrozate that is high in carbohydrates is produced. This hydrozate requires low pH processing. In some embodiments of the present invention, the first extraction liquid and the last extraction solid of this phase is the finished coproduct. Phase II may involve continuous or batch processing depending on operational factors such as the biomass being processed and the processing time requirements. Once acid treatment is completed, the saturated material is pressed. For purposes of this specification, press includes any action taken on the saturated material (acid treated biomass) to enhance the extraction of liquid precursor hydrozate. This may include, but is not limited to, mechanical pressing, cetrifuge, gravity, and the like. When pressed, the treated biomass yields a liquid precursor hydrozate 415 that is placed in a vessel or other storage device for later processing and shipment to a user of the liquid, such as a biorefinery. The solids remaining may then be used for applications such as, but not limited to, enhanced animal feed, enhanced sweet animal feed 409, or they may be further processed in Phase III. Phase III involves an enzymatic treatment and press 405. This third phase is an optional phase of the multiple phase apparatus and may or may not be required depending on the biomass being produced and the co-products being required or requested. This is the last phase of the multiple phase apparatus that may or may not use a different process design than phase I and or II. The primary objective of Phase III is to hydrolyze and extract carbohydrates that require processing at a different pH level and or temperature, and that also require digesting enzymes and or microbes to support hydrolyzing of carbohydrates to produce the hydrozate. Enzymes may include, but are not limited to enzymes, such as Accellerase© 1500 by Genencor, a Danisco Divison, headquartered in Rochester, N.Y., USA, Accellerase® XY, XC, and BG by Genencor, a Danisco Divison, headquartered in Rochester, N.Y., USA, BAN® by Novozymes A/S of Bagsvaerd, Denmark, Liquozyme® by Novozymes A/S of Bagsvaerd, Denmark, Spirizyme® by Novozymes A/S of Bagsvaerd, Denmark, Viscozyme® by Novozymes A/S of Bagsvaerd, Denmark, and CornBuster™ by C5·6 Technologies, Inc. of Middleton, Wis. 53562.

As with Phase I and Phase II this Phase may involve multiple cycles. A first cycle uses an aqueous solution with pH adjusting additives along with any required digesting enzymes and or microbes as its liquid fraction or prior cycle extraction liquid along with additional pH adjusting additives and any required digesting enzymes and or microbes as its liquid fraction. The solid fraction biomass used in Phase III is typically the solids coproduced in Phase II. In many embodiments of the present invention, the first extraction liquid and the last extraction solid of this phase are the finished coproduct objectives. Phase III can be a batch process or a continuous process depending on the biomass being processed and other variables. Once enzymatic treatment is completed, the saturated material is pressed. For purposes of this specification, press includes any action taken on the saturated material (acid treated biomass) to enhance the extraction of liquid precursor hydrozate. This may include, but is not limited to, mechanical pressing, cetrifuge, gravity, and the like. When pressed, the treated biomass yields a liquid precursor hydrozate 417 that is placed in a vessel or other storage device for later processing and shipment to a user of the liquid, such as a biorefinery. The solids remaining are high lignin materials that may be used for a wide variety of applications such as absorbent media, animal or human food and food additives, building products such as composite boards and sheets, animal bedding, combustible fuels such as burning pellets, adhesive and plastic additives, bio-plastics, soil additives, and the like.

Figure 5:
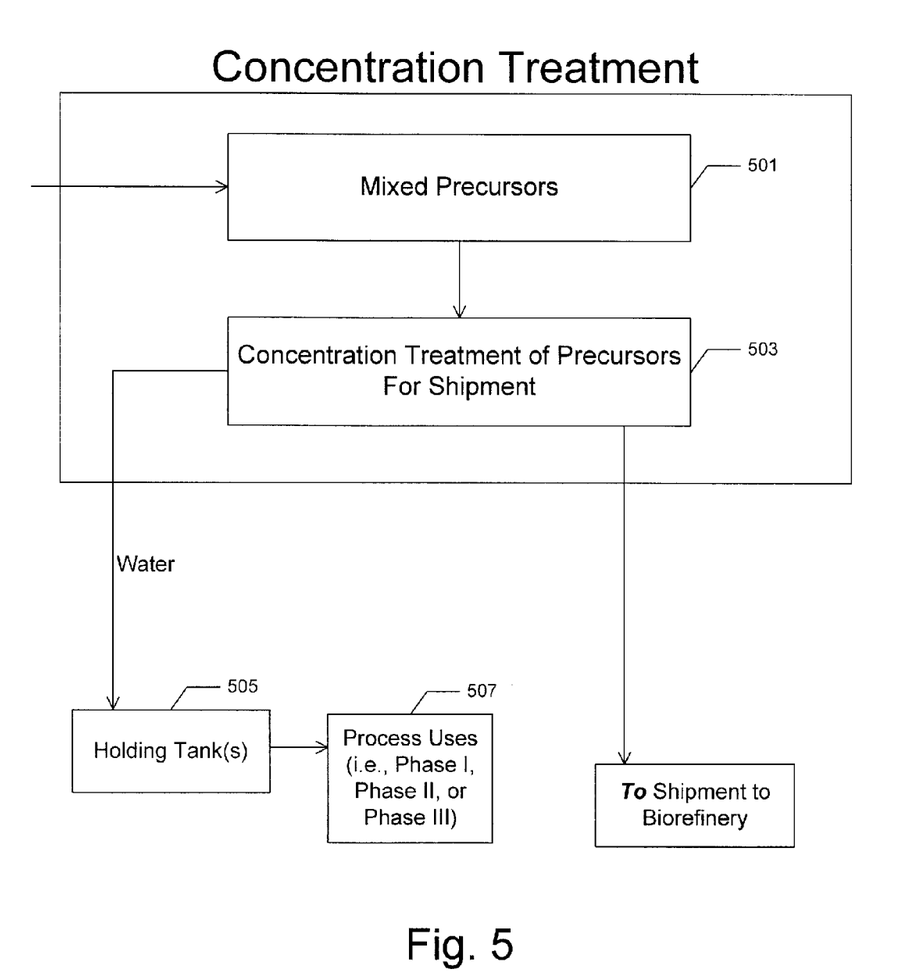
FIG. 5 is a diagram that shows the concentration of liquid precursors.

The liquid precursor hydrozates from each phase may be combined in a vessel, appropriate container, batch or continuous process and will receive a concentration treatment, as described by way of FIG. 5. In some embodiments of the present invention, further treatment of the liquid precursor hydrozate may take place, including, for example, the addition of enzymes such as Accellerase© 1500 by Genencor, a Danisco Divison, headquartered in Rochester, N.Y., USA, Accellerase® XY, XC, and BG by Genencor, a Danisco Divison, headquartered in Rochester, N.Y., USA, BAN® by Novozymes A/S of Bagsvaerd. Denmark, Liquozyme® by Novozymes A/S of Bagsvaerd, Denmark, Spirizyme® by Novozymes A/S of Bagsvaerd, Denmark, Viscozyme® by Novozymes A/S of Bagsvaerd, Denmark, and CornBuster™ by C5·6 Technologies, Inc. of Middleton, Wis. 53562.

Turning now to FIG. 5, the mixed precursors 501 (liquid precursor hydrozates) may receive further concentration treatment 503 prior to shipment. This step involves removing some water from the mixed precursors and may optionally include treatment such as chemical treatment, biomaterial treatment, and the like. Concentration involves a water extraction device. Water extraction devices include, but are not limited to, reverse osmosis membranes and systems, applied heat systems, ultra filtration systems, nano filtration systems, and other such devices that will remove and further concentrate the liquid precursor hydrozates. The water that has been removed by the water extraction device is placed in a holding tank 505 or other retention device and may be reused for other process uses 507. Once concentration is completed, the concentrated liquid precursor hydrozate is ready for shipment to a biorefinery for fermentation, distillation and reduction to an alcohol such as ethanol. Concentrated liquid precursor hydrozate provides reduced shipping costs, material handling costs, and the like.

Figure 6:
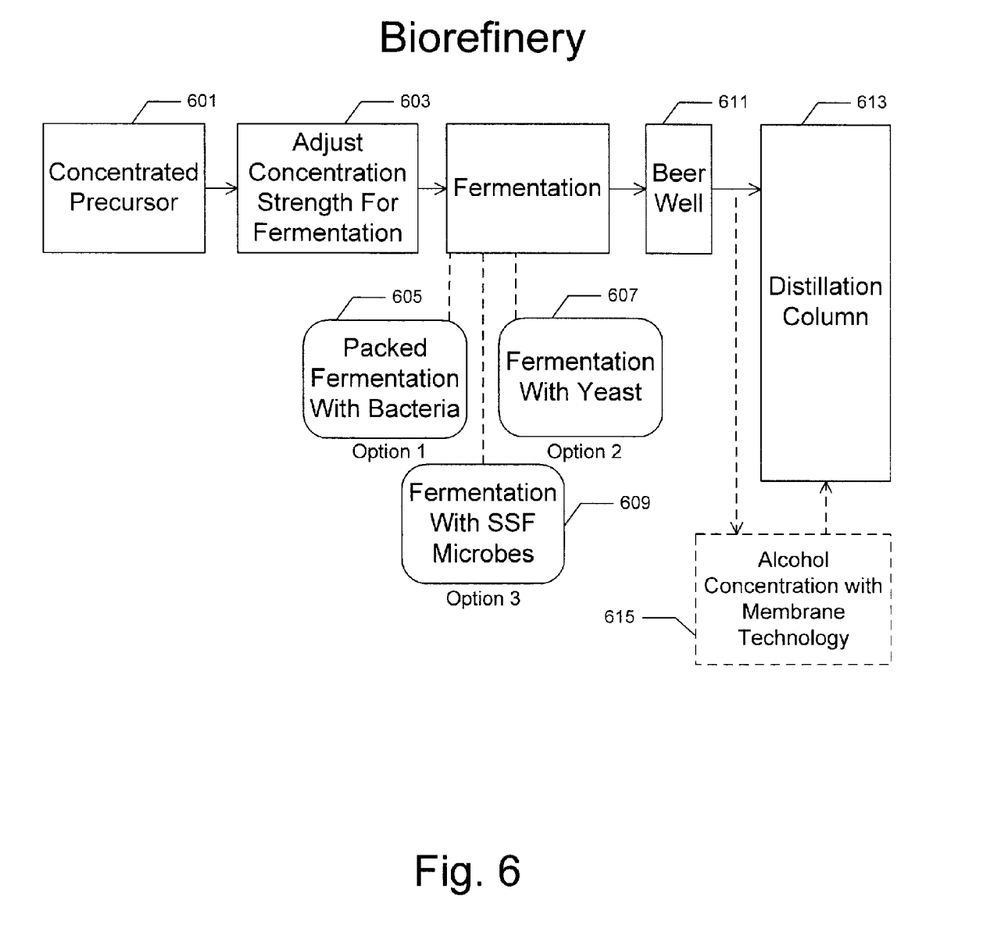
FIG. 6 is a diagram depicting processes at a biorefinery.

FIG. 6 depicts some typical processes at a biorefinery that uses the liquid precursor hydrozate for production of alcohol such as ethanol. The concentrated precursor 601 (concentrated liquid precursor hydrozate) may have water added such that the concentration strength for fermentation 603 is optimized. Fermentation may take place using several options. Option 1 used packed fermentation with bacteria 605. In packed fermentation, solid material is added to the liquid precursor hydrozate, the fermenter containing structures to increase surface area in a given volume to provide increased surface area for microbes or bacteria to inhabit. An example of a novel solid material that may be used for packed fermentation is the packed fermenter structure of FIG. 10. Such a structure can be added to a fermentation vessel or process in quantity, and may be reused. Another option for fermentation is Option 2, fermentation with yeast 607. Such fermentation is known to those skilled in the art, and may include a fermentation vessel with a water lock or other similar device to allow carbon dioxide to exit without allowing entry of ambient air. Another option, Option 3, involves fermentation with Simultaneous Sacrification and Fermentation (SSF) microbes. An example of such a microbe is Clostridium Phytofermentans, produced by QTEROS of Marlborough, Mass., USA as the Q Microbe. Once fermentation is completed and the sugars contained in the liquid precursor hydrozate have been converted to alcohol, the fermented liquid is transferred to a beer well 611 or similar structure. The fermented liquid (beer) is then sent to a distillation column where alcohol is boiled from the fermented liquid and condensed, leaving the higher boiling point water behind.

Optionally, to reduce energy costs, alcohol concentration 615 may be performed by way of membrane technology systems. The resulting product of the biorefinery is alcohol such as ethanol, produced from the liquid precursor hydrozate.

Figure 7:
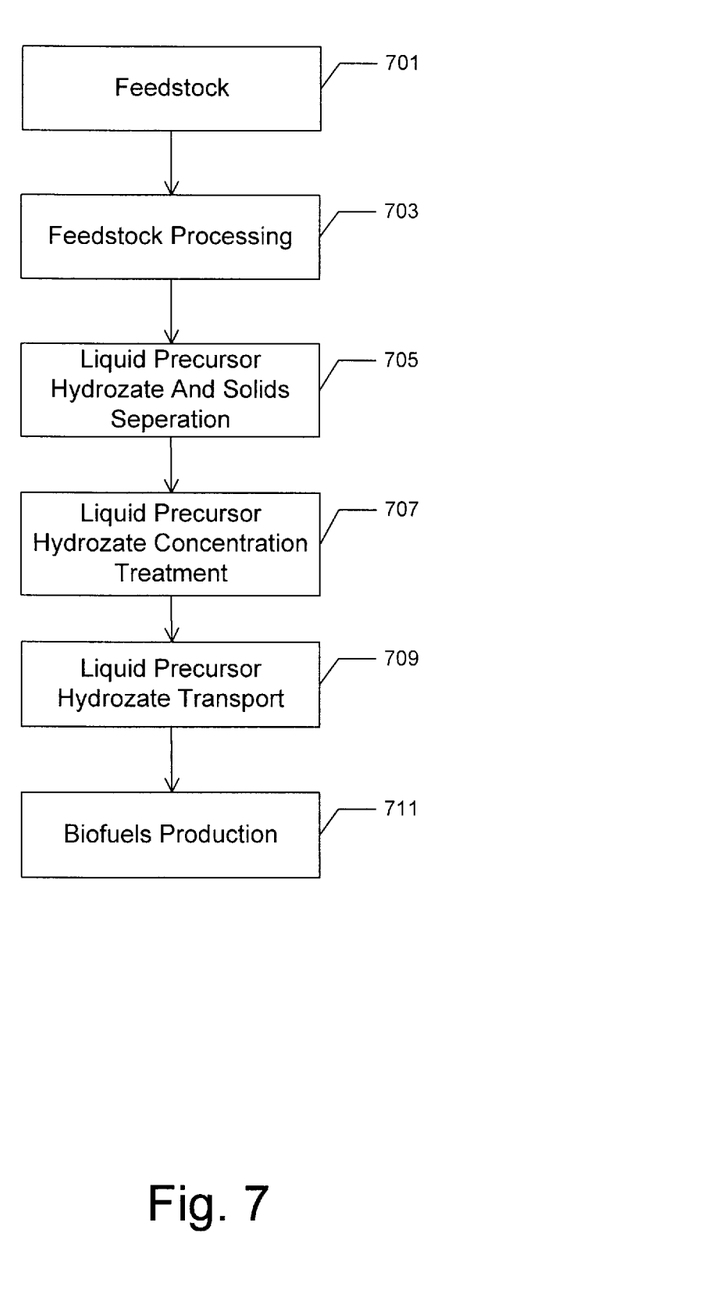
FIG. 7 is a diagram showing the major steps in producing biofuels according to the present invention.

To illustrate the major steps in producing alcohol according to the present invention, one may refer to FIG. 7. The process begins with the provision of feedstock in step 701. Feedstock, as previously defined herein, is biomass, and as has been stated previously, the terms feedstock and biomass are used interchangeably throughout this specification. Feedstock is processed in step 703. Feedstock processing has been previously described by way of FIGS. 2, 3, and 4, and includes, but is not limited to, harvest, pretreatment, storage, ensiling, mechanical processing, secondary destruction and processing, application of inoculates and application of chemicals. Liquid precursor hydrozate, and solids, also known as solid precursor hydrozate, are separated in step 705 as previously described by way of FIG. 4. The separation is performed using techniques such as, but not limited to, mechanical pressing, pressing, centrifuge, gravity, and the like. These actions are generically and collectively referred to as "press" in this specification. In step 707, the liquid precursor hydrozate undergoes a concentration treatment, as previously described by way of FIG. 5. Concentration treatment includes the removal of water as well as optionally the addition of chemicals and or biomaterials. The liquid precursor hydrozate is then transported from a distributed feedstock processing location in step 709 to a biorefinery for the production of an alcohol such as ethanol in step 711.

Figure 8:
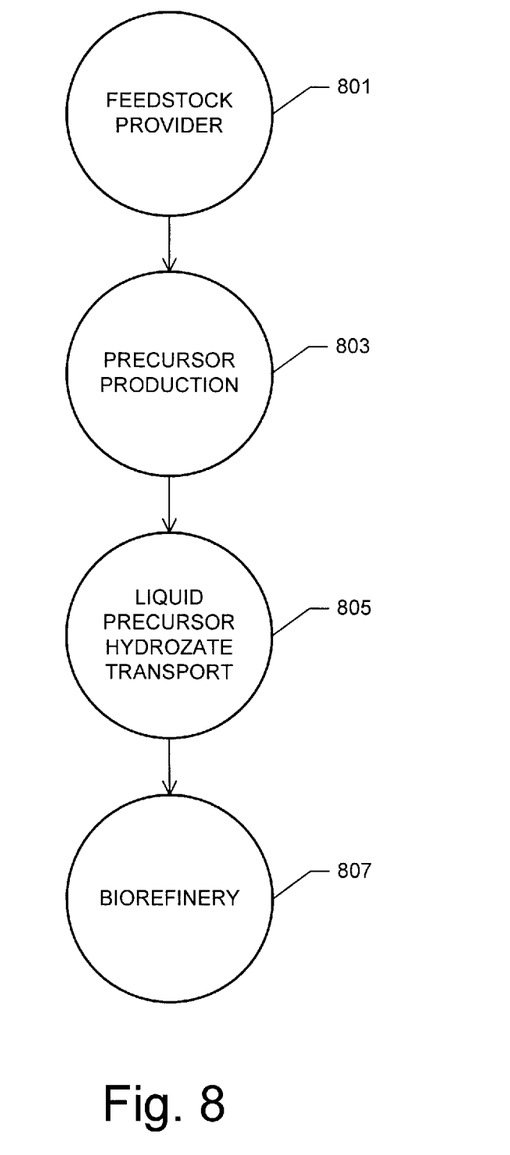
FIG. 8 is a diagram showing major process components of the present invention.

FIG. 8 is a diagram showing major process components of the present invention. A feedstock provider 801 may be a farmer or agricultural operations or processing operator, a manufacturer of food or material, or any other provider of biomass. Precursor Production 803 includes the production of both liquid and solid precursor hydrozates. Precursor Production has been previously described by way of FIGS. 1, 2, 3, 4, and 5, and includes, but is not limited to, harvest, post harvest processing, pretreatment, storage, ensiling, mechanical processing, secondary destruction and processing, application of inoculates and application of chemicals, separation of liquid precursor hydrozates from solid precursor hydrozates, and concentration treatment. Transportation of liquid precursor hydrozate in step 805 to a biorefinery 807 will then result in fermentation and distillation of the liquid precursor hydrozate at the biorefinery.

Figure 9:
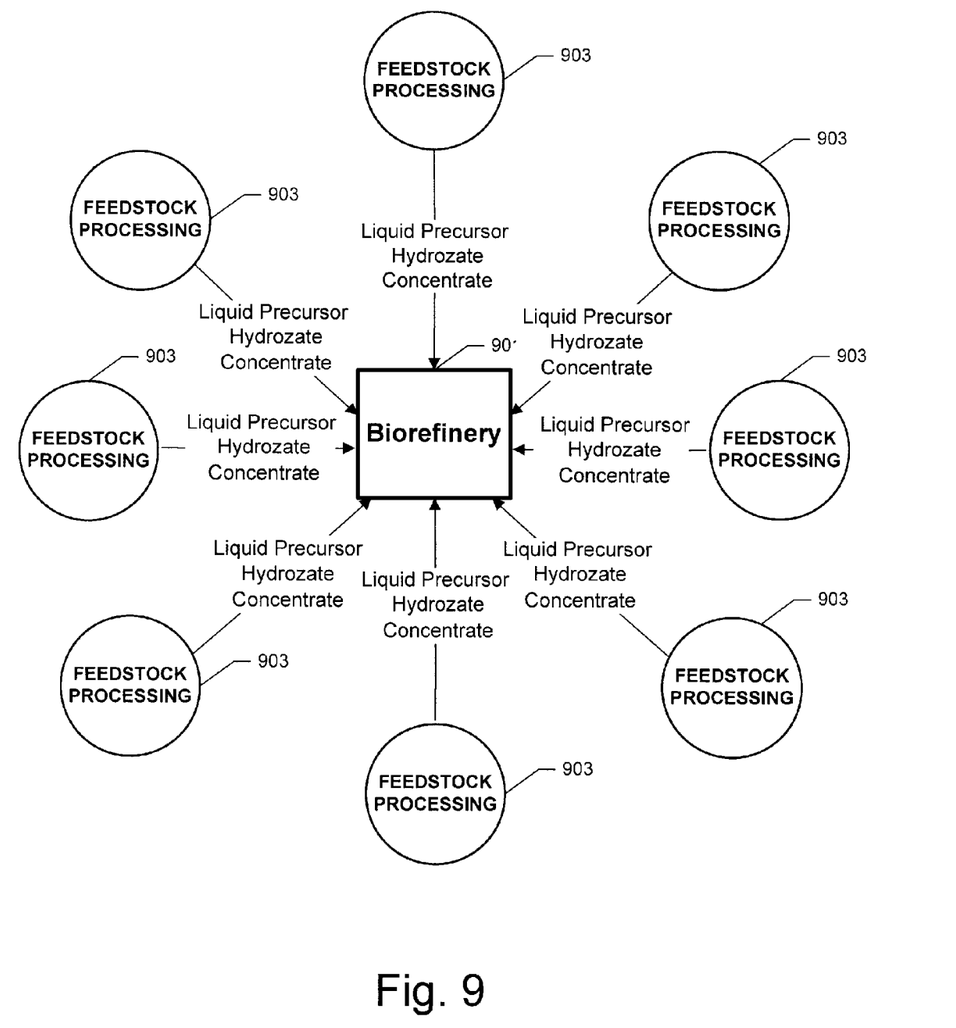
FIG. 9 depicts a distributed feedstock processing and central biorefinery system.

FIG. 9 depicts a distributed feedstock processing and central biorefinery system according to the present invention. As depicted, feedstock processing 903 takes place at a plurality of distributed sources, resulting in transportation of liquid precursor hydrozate to a central biorefinery 901 for the fermentation and distillation of the liquid precursor hydrozate, resulting in alcohol such as ethanol. The liquid precursor may be concentrated and may have some amount of water removed or added, but may still be referred to generically as liquid precursor concentrate regardless of the amount of water removed or added. The operation of a biorefinery using the products and processes of the present invention has been previously described by way of FIG. 6.

Figure 10:
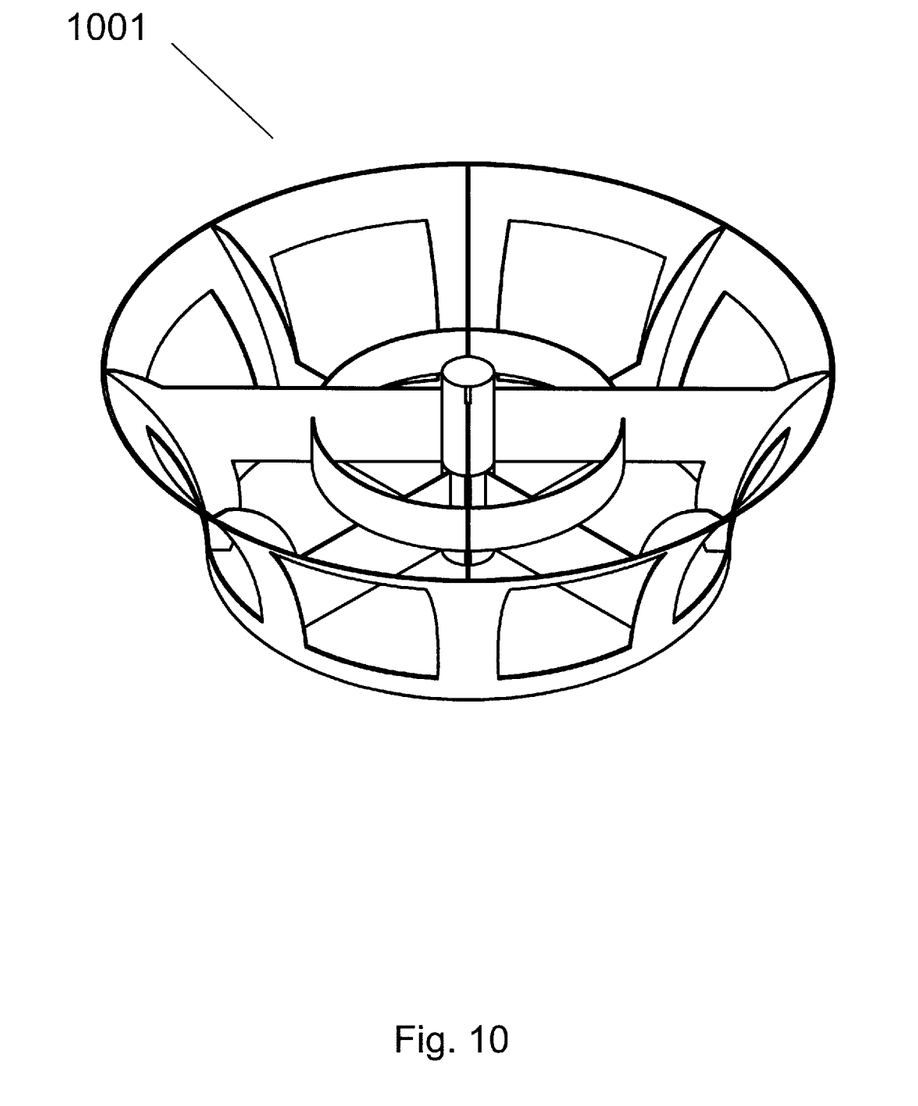
FIG. 10 is a perspective view of an exemplary packed fermenter structure.
Figure 11:
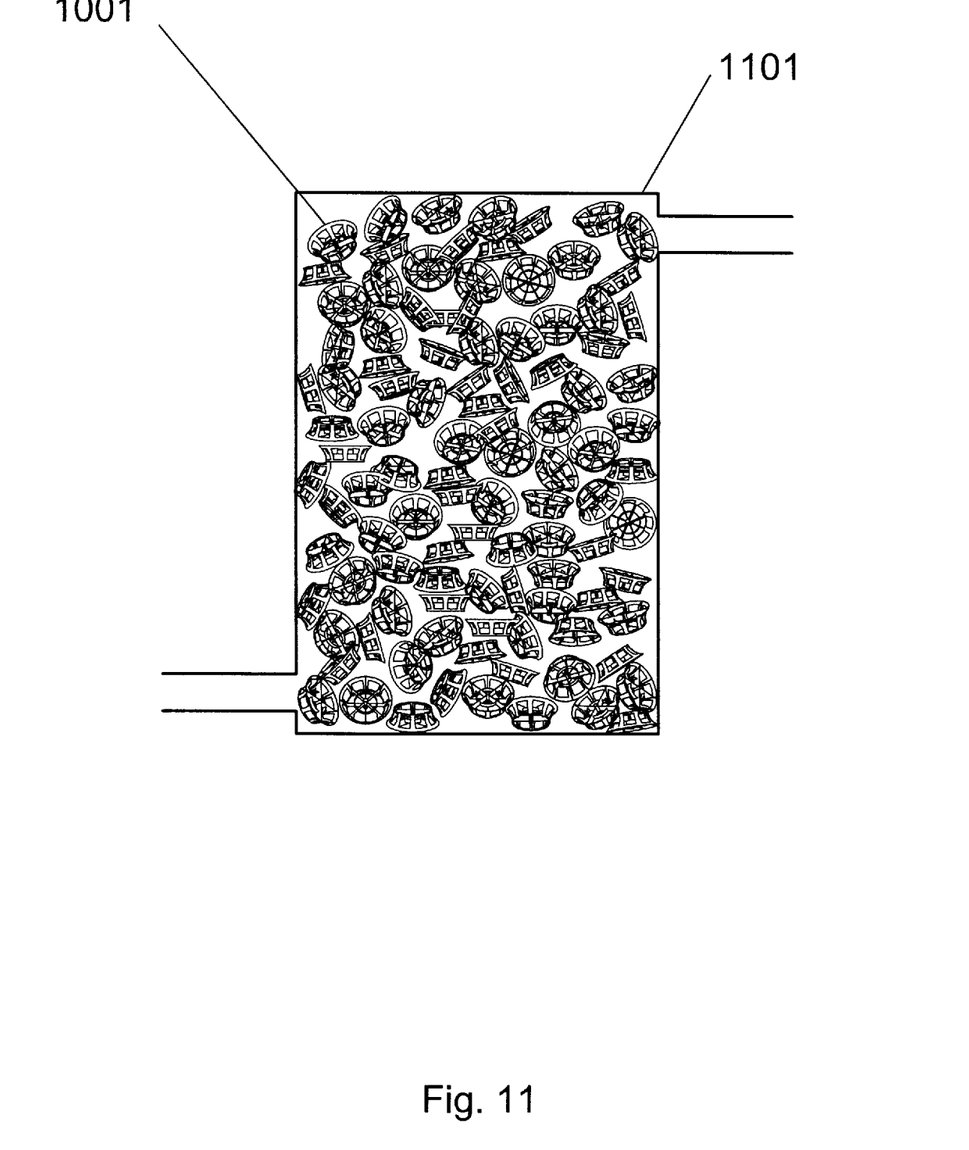
FIG. 11 is a cross sectional view of a vessel containing packed fermenter structures.

One of the operations of a biorefinery is the fermentation of the liquid precursor hydrozate prior to distillation. Fermentation is an anaerobic process used primarily by yeasts where sugars such as glucose, fructose and sucrose are converted into cellular energy with alcohol and carbon dioxide as waste products for the yeast. In traditional fermentation, biomass is present along with liquid components. The presence of biomass serves to increase surface area available to microbes such as yeasts. The present invention uses liquid precursor hydrozate for fermentation. This liquid does not contain large surface area biomass structure. FIG. 10 depicts a packed fermenter structure 1001. Such a packed fermenter structure serves to provide a high surface area structure for the growth of microbes such as yeast, bacteria, and the like. The packed fermenter structure 1001 has a circular shape, but other geometries may be used without departing from the spirit and broad scope of the present invention. The packed fermenter structure may be made from a plastic such as polyethylene, polypropylene, or the like. The packed fermenter structure may also be made from biomaterials such as biomass fibers, polylactide, and the like. The packed fermenter structure may also be made from a metal such as stainless steel. In the case of a plastic packed fermenter structure, plastic additives such as fibers or spheres may optionally be added to further increase surface area. The plastic fermenter structure may vary in size, an example of a size range being 1 to 5 inches in diameter. FIG. 11 depicts the packed fermenter structures in use in a processing vessel 1101. The packed fermenter structures 1001 are randomly distributed throughout the vessel. The vessel may be of varying size, capacity, geometry, or may be a batch or continuous arrangement. Such a structure improves the efficiency of the fermentation process given the novel systems and methods described herein.

It is, therefore, apparent that there has been provided, in accordance with the various objects of the present invention, a multi-phase apparatus for the hydrolyzation of ensiled biomass and related systems and methods for producing alcohol from liquid precursors produced by the multi-phase apparatus. While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification drawings and claims herein.

What is claimed is:

1. A method for producing a liquid precursor hydrozate and a solid precursor hydrozate, the method comprising:
    treating a biomass composition comprising cellulose, hemicellulose and/or lignocellulose with an acid in an acid treatment vessel to hydrolyze the cellulose, hemicellulose, and/or lignocellulose of the biomass composition, pressing the biomass in the acid treatment vessel, removing water from the acid treated biomass composition;
    heat treating the dewatered, acid treated biomass composition with hot water in a heat treatment vessel;
    pressing the heat treated biomass using a separator operatively coupled to the heat treatment vessel to separate a liquid precursor hydrozate from a solid precursor hydrozate; and
    performing the preceding steps with a process control system.

2. The method of claim 1, further comprising concentrating the liquid precursor hydrozate with a water extraction device.

3. The method of claim 2, wherein the water extraction device is a reverse osmosis system.

4. The method of claim 2, wherein the water extraction device is an applied heat system.

5. The method of claim 2, wherein the water extraction device is an ultra filtration system.

6. The method of claim 2, wherein the water extraction device is a nano filtration system.

7. The method of claim 1, wherein the method is conducted in a portable apparatus.

8. The method of claim 1, wherein the separator is a mechanical press.

9. The method of claim 1, wherein the separator is a centrifuge press.

10. The method of claim 1, wherein the separator is a gravity press.

11. The method of claim 1, further comprising treating the liquid precursor hydrozate with one or more enzymes in an enzymatic treatment device.

12. The method of claim 1, further comprising treating the solid precursor hydrozate with one or more enzymes in an enzymatic treatment device.

13. The method of claim 1, wherein the biomass composition comprising cellulose, hemicellulose and/or lignocellulose further comprises hard grains, starches, or a combination thereof.

14. The method of claim 1, wherein the biomass composition comprising cellulose, hemicellulose, and/or lignocellulose is corn stover, cereal straws, sugarcane bagasse, sawdust, paper pulp, waste materials, switchgrass, animal feed, paper, cardboard, or a combination thereof.

15. The method of claim 1, wherein the acid is sulfuric acid.

16. The method of claim 1, wherein the acid is muriatic acid.

17. The method of claim 1, wherein the acid is hydrochloric acid.

18. The method of claim 1, wherein the biomass composition comprising cellulose, hemicellulose, and/or lignocellulose is an ensiled biomass.

* * * * *